United States Patent [19]

Brewer

[11] Patent Number: 4,879,276

[45] Date of Patent: Nov. 7, 1989

[54] METHOD FOR REDUCING SERUM URIC ACID LEVELS

[75] Inventor: Arthur D. Brewer, Puslinch, Canada

[73] Assignee: Uniroyal Chemical Ltd./Uniroyal Chemical Ltee, Don Mills, Canada

[21] Appl. No.: 142,626

[22] Filed: Jan. 11, 1988

Related U.S. Application Data

[63] Continuation-in-part of Ser. No. 919,922, Oct. 16, 1987, abandoned, which is a continuation of Ser. No. 827,479, Feb. 5, 1986, abandoned, which is a continuation of Ser. No. 699,720, Mar. 21, 1985, abandoned, which is a continuation of Ser. No. 65,267, Oct. 26, 1984, abandoned, which is a continuation-in-part of Ser. No. 562,693, Dec. 19, 1983, abandoned.

[51] Int. Cl.⁴ .................. A61K 31/70; A61K 31/505; A61K 31/515
[52] U.S. Cl. ........................ 514/43; 514/50; 514/269; 514/270
[58] Field of Search .................... 514/43, 50, 269, 270

[56] References Cited

U.S. PATENT DOCUMENTS

| | | | |
|---|---|---|---|
| 4,034,093 | 7/1977 | Klemm et al. | 514/269 |
| 4,762,830 | 8/1988 | Strurm et al. | 514/270 |

Primary Examiner—John W. Rollins
Attorney, Agent, or Firm—J. A. Shedden

[57] ABSTRACT

Method for reducing uric acid levels in mammals, comprising administering compounds having the formula:

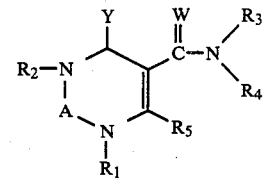

wherein A is selected from the group consisting of

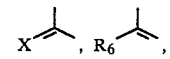

and $-CH_2-$; X is oxygen or sulfur; $R_6$ is hydrogen, an alkoxy group having from one to four carbon atoms, or alkylthio, amino, dialkylamino, or $NHR_7$ wherein $R_7$ is alkyl, aryl or arylamino, the alkyl moieties of which have from 1 to 12 carbon atoms;

$R_1$ and $R_2$ may each independently be hydrogen; alkyl, aryl, aralkyl, aralkenyl or aralkynyl, the alkyl, alkenyl or alkynyl moieties of which have from one to six carbon atoms, or a carbohydrate residue;

$R_3$ is hydrogen, $C_1$-$C_4$ alkyl or aryl;

$R_4$ is phenyl, naphthyl, benzyl, naphthylmethyl, thienyl, thienylmethyl or pyridyl; or phenyl, naphthyl, benzyl, naphthylmethyl, thienyl, thienylmethyl or pyridyl substituted with one or more of the following groups: hydroxy; halo; alkyl, alkoxy, alkylthio, haloalkyl or haloalkoxy having from one to four carbon atoms; carboxy; alkoxycarbonyl having from two to five carbon atoms; nitro; cyano; aryl; aryloxy; arylthio; benzyl; benzyloxy; naphthylmethyl; naphthyl; methyloxy; thienyl; or thienylmethyl;

$R_5$ is hydrogen or ZH;

W, Y and Z may each independently be oxygen or sulfur; and the pharmacologically acceptable addition salts thereof.

2 Claims, No Drawings

METHOD FOR REDUCING SERUM URIC ACID LEVELS

This application is a continuation-in-part of U.S. patent application Ser. No. 919,922 filed Oct. 16, 1987, now abandoned; which is a continuation of U.S. patent application Ser. No. 827,479 filed Feb. 5, 1986, now abandoned; which is a continuation of U.S. patent application Ser. No. 699,720 filed Mar. 21, 1985, now abandoned; which is a continuation of U.S. patent application Ser. No. 665,267 filed Oct. 26, 1984, now abandoned; which is a continuation-in-part of U.S. patent application Ser. No. 562,693 filed Dec. 19, 1983, now abandoned.

TECHNICAL FIELD

This invention relates to a method for reducing serum uric acid levels in mammals, employing certain 5-pyrimidinecarboxamides as active agents.

BACKGROUND OF THE INVENTION

The presence of uric acid is implicated in several human disorders, including gout. Gout is a metabolic disease marked by a painful inflammation of the joints, deposits of urates in and around the joints, and usually an excessive amount of uric acid in the blood. Gout is generally treated in one of four ways:

(1) uricosuric agents to increase renal function (enhanced fluid elimination);
(2) colchicine, a microtubule inhibitor;
(3) non-steroidal anti-inflammatory agents, e.g., indomethacin; and
(4) allopurinol, a xanthine oxidase inhibitor.

5-pyrimidinecarboxamides, and particularly 5-carboxamides of barbituric acid, have previously been described as useful for various therapeutic purposes. For example, Takeda Pharmaceutical Industries' Japanese Patent Publication No. 1,445/64, published on Feb. 14, 1964, suggests the use of compounds of the formula:

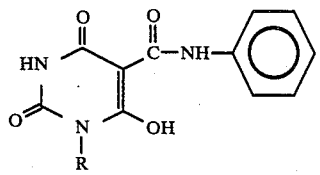

i.e., 5-phenylcarbamoylbarbituric acid (wherein R is hydrogen) and 1-substituted-phenylcarbamoylbarbituric acids (wherein R is alkyl or phenyl), as potential anti-cancer agents.

Analogs of similar barbituric acid derivatives have also been described in the literature. Thus, N-substituted-2-amidocarbonylthiobarbituric acids of the formula:

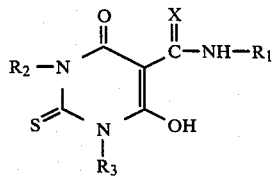

wherein $R_1$ is alkyl, alkenyl, various substituted alkyl, alkenyl or carbonyl, or optionally substituted aryl or aralkyl; $R_2$ and $R_3$ are each independently alkyl, alkenyl, cycloalkyl, aryl, aralkyl or hydrogen, provided that not more than one of $R_2$ and $R_3$ is hydrogen; and X is oxygen or sulfur, are disclosed in Bayer AG German Offen. No. 24 05 732 and in Kramer et al., U.S. Pat. No. 3,961,061 granted on June 1, 1976. These thiobarbituric acid derivatives are described as possessing insecticidal, acaricidal, fungicidal and bactericidal properties.

Other 5-carboxamido-substituted thiobarbituric acids such as:

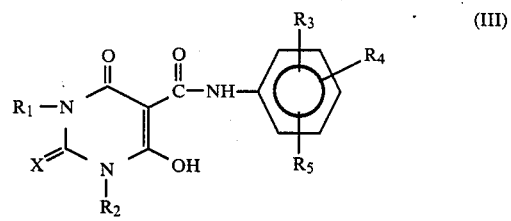

wherein X is oxygen or sulfur; $R_1$ and $R_2$ may each by alkyl, alkenyl, benzyl or unsubstituted or substituted phenyl; $R_3$ may be halogen, nitro or trihalomethyl; $R_4$ is hydrogen, halogen or trihalomethyl; and $R_5$ is hydrogen, halogen, methyl or methoxy, are also described in he patent literature. Such compounds are disclosed in Ciba-Geigy European Patent Publication No. 74,335 and in DeSousa et al., U.S. Pat. No. 4,283,444 granted on Aug. 11, 1981, as useful for protecting keratinous materials, especially wool, from insect attack.

More recently, it has been disclosed in Brewer et al. U.S. Pat. No. 4,634,707, owned by the assignee of the present invention, that certain 5-carboxamide-2-thiobarbituric acid derivatives, viz., compounds of the formula:

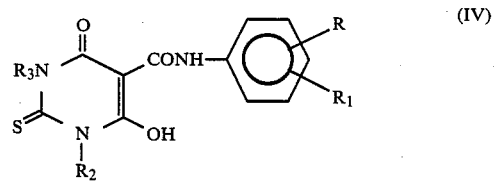

wherein R is hydrogen, 2 or 3-halo, 2-methyl, 4-fluoro, 4-($C_1$-$C_6$ alkoxyl), 2 or 4-trifluoromethyl, or hydroxyl, and $R_1$ is hydrogen; or R is 2-fluoro and $R_1$ is 4-fluoro; or R is 2-methoxy and $R_1$ is 5-methyl; and $R_2$ and $R_3$ are hydrogen atoms or carbohydrate residues, and the pharmacologically acceptable addition salts thereof, induce regression or inhibit the growth of leukemia and various malignant tumors in mammals.

The use of yet other 5-pyrimidinecarboxamides as anti-leukemia and anti-tumor drugs is disclosed in Brewer et al. U.S. Pat. No. 4,636,508, also owned by the present assignees.

It is among the objects of the present invention to provide a therapeutic method for reducing serum uric acid levels in man or other mammals, utilizing the preceding and other 5-pyrimidinecarboxamide derivatives. Other objects and advantages of the invention will be apparent from the following detailed description of preferred embodiments thereof.

SUMMARY OF THE INVENTION

In accordance with the present invention, it has been found that serum uric acid levels may be reduced by administering to a patient a 5-pyrimidinecarboxamide of the formula:

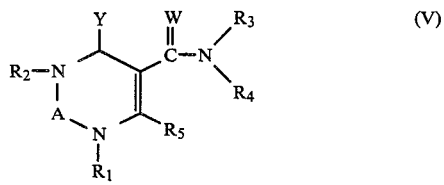

(V)

wherein
A is selected from the group consisting of

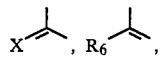

and —CH$_2$—; X is oxygen or sulfur; R$_6$ is hydrogen, an alkoxy group having from one to four carbon atoms, or alkylthio, amino, dialkylamino, or NHR$_7$ wherein R$_7$ is alkyl, aryl or arylamino, the alkyl moieties of which ave from 1 to 12 carbon atoms;

R$_1$ and R$_2$ may each independently be hydrogen; alkyl, aryl, aralkyl, aralkenyl or aralkynyl, the alkyl, alkenyl or alkynyl moieties of which have from one to six carbon atoms, or a carbohydrate residue;

R$_3$ is hydrogen, C$_1$-C$_4$ alkyl or aryl;

R$_4$ is phenyl, naphthyl, benzyl, naphthylmethyl, thienyl, thienylmethyl or pyridyl; or phenyl, naphthyl, benzyl, naphthylmethyl, thienyl, thienylmethyl or pyridyl substituted with one or more of the following groups: hydroxy; halo; alkyl, alkoxy, alkylthio, haloalkyl or haloalkoxy having from one to four carbon atoms; carboxy; alkoxycarbonyl having from two to five carbon atoms; nitro; cyano; aryl; aryloxy; arylthio; benzyl; benzyloxy; naphthylmethyl; naphthyl; methyloxy; thienyll or thienylmethyl;

R$_5$ is hydrogen or ZH;

W, Y and Z may each independently be oxygen or sulfur; and the pharmacologically acceptable addition salts thereof.

A preferred class of the 5-pyrimidinecarboxamides useful herein comprise the phenylcarboxamides of 2-barbituric acid or 2-thiobarbituric acid, of the formula:

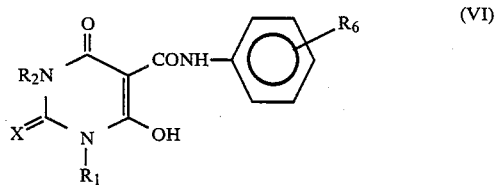

(VI)

wherein
R$_1$, R$_2$ and X are as defined above; and
R$_6$ is at least one substituent selected from the group consisting of hydrogen; halogen; alkyl, alkenyl, alkynyl, alkoxy, aryl, aralkyl, aralkenyl, aralkynyl or aralkoxy, the alkyl, alkenyl, alkynyl or alkoxy moieties which have from one to six carbon atoms; and the pharmaceutically acceptable addition thereof.

Particularly preferred among the foregoing c pounds is the compound in which R$_1$, R$_2$ and R$_6$ ar hydrogen and X is thioxo, viz., 5-(phenylcarboximi 2-thiobarbituric acid [also known as 1,2,3,4-tetrahy 6-hydroxy-4-oxo-N-phenyl-2-thioxo-5-pyrimidineca boxamide, or merbarone]:

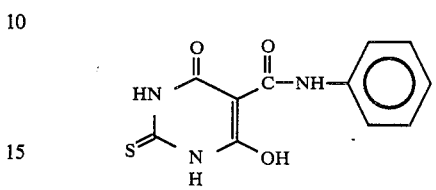

Addition salts of the above mentioned compou may be formed with a variety of pharmacologic acceptable organic and inorganic salt-forming reage Useful addition salts may thus be formed by admix of the organic acid with one equivalent of a base, an organic amine such as triethylamine or N-me glucamine, and inorganic cations such as sodium, po sium or the like. The addition salts of the organic a of the invention are, in general, crystalline solids wl are relatively insoluble in both polar solvents suc: water, methanol and ethanol, and non-polar org: solvents such as diethylether, benzene, toluene and like. They are somewhat soluble in aprotic solv such as dimethylformamide and dimethylsulfoxide.

On the other hand, when R$_1$ or R$_2$ is a carbohyd residue it may be furanosyl (e.g., glucopyranosyl), t. deoxy derivatives, or their aliphatic analogs (e.g., droxyalkoxyalkyl or polyhydroxyalkyl groups hav from 2 to 12 carbon atoms in each of the alkoxy alkyl moieties thereof, such as 2-hydroxyethoxymei or 2,3-dihydroxypropyl. As used herein, the term "t bohydrate residue" is intended to refer to those cy and acyclic groups which form pyrimidine nucleos or pseudo nucleosides, e.g., materials including both cyclic and acyclic groups specified hereinabove.

The 5-carboxamido or thiocarboxamido 2-barbit acid derivatives can exist in the forms illustratec Formulas V-VII or in any of their tautomeric for For ease of understanding, the compounds of the inv tion will only be illustrated herein in the forms show Formulas V-VII but will be understood to embrace tautomers thereof, or tautomeric mixtures.

The specific mechanism by which the therape agent of the present invention reduces serum uric a levels is not presently known. It is not believed to p cipally act by inhibiting xanthine oxidase activity. 1 is it known whether the 5-pyrimidinecarboxamides to inhibit the formation of uric acid or to destroy pr ously formed uric acid. Whatever the particular r tion mechanism, the method of the present inven comprehends the reduction of serum uric acid level: administration of the specified 5-pyrimidinecarbc mides.

The 5-pyrimidinecarboxamides useful herein ma prepared by procedures known in the art, e.g., by procedures described in the aforesaid prior patents, Kramer et al. U.S. Pat. No. 3,961,061; De Sousa e U.S. Pat. No. 4,283,444; and Brewer et al. U.S. Pat. I 4,634,707 and 4,636,508. The particularly prefer species, merbarone, may be prepared as describec Example 1 of the aforesaid Brewer et al. U.S. Pat. No. 4,634,707.

Administration of the 5-pyrimidinecarboxides to humans in amounts ranging from 100 to 1,000 mg/m$^2$ is effective in decreasing serum uric acid levels. The dosage level may, of course, be adjusted to provide optimum therapeutic response. For example, several divided doses may be administered daily, or the dose may be proportionately reduced, as indicated by the exigencies of the therapeutic situation.

The active compounds may suitably be administered parenterally, intraperitoneally, intravenously or orally. Solutions or dispersions of the active compounds can be prepared in water, suitably mixed with the surfactants such as hydroxypropylcellulose. Dispersions can also be prepared in glycerol, liquid polyethylene glycol, and mixtures thereof, and in oil. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. For such uses the form must be sterile and must be fluid to the extent necessary to provide easily syringability. It must be stable under the conditions of manufacture and storage and must be preserved against the contaminating action of microorganisms such as bacteria and fungi.

The carrier can be a solvent or dispersing medium containing, for example, water, ethanol, a polyol (for example, glycerol, propylene glycol, and liquid polyethylene glycol, or the like), suitable mixtures thereof, and vegetable oils. The proper fluidity can be maintained, for example, by the use of a coating such as lecithin, by the maintenance of the required particle size in the case of a dispersion, and by the use of surfactants. Prevention of the action of microorganisms can be insured by varius anti-bacterial and anti-fungal agents, for example, paraben, chlorobutanol, phenol, sorbic acid, thimerosal, or the like. In many cases, it may be preferable to include isotonic agents, for example, sugars or sodium chloride, in the dosage form. Prolonged absorption of the injectable formulations can be brought about by incorporating agents delaying absorption, for example, aluminum monostearate and gelatin, therein.

Sterile injectable solutions are prepared by incorporating the active compound in the appropriate solvent, in admixture with various of the other ingredients enumerated above, as required, followed by filtered sterilization. Generally, dispersions are prepared by incorporating the sterilized active ingredient in a sterile vehicle which contains the dispersing media and other required ingredients. When, on the other hand, sterile powders are used to prepare sterile injectable solutions, it is preferred to subject a sterile, filtered solution of the desired ingredients to vacuum drying or freeze drying, yielding a powder of the active ingredient plus any additional desired ingredients.

As used herein, "pharmaceutically acceptable, substantially non-toxic carrier or excipient" includes solvents, dispersing media, coatings, anti-bacterial and anti-fungal agents, isotonic and absorption-delaying agents, and the like. The use of such media and agents as carriers or excipients for pharmaceutically active substances is well known in the art. Except insofar as any conventional media or agent is incompatible with the active ingredient or toxic, its use in the therapeutic formulations of the invention is contemplated. Supplementary active ingredients can also be incorporated in the therapeutic compositions.

It may be advantageous to formulate the composition of the invention in unit dosage forms for ease of administration and uniformity of dosage. A unit dosage form, as used herein, refers to a physically discrete unit suitable for use as a unitary dosage for the mammalian subject to be treated; each unit contains a predetermined quantity of active material calculated to produce the desired therapeutic effect, in association with the required pharmaceutically acceptable carrier. Specifications for unit dosage forms are dictated by and directly depend on (a) the unique characteristics of the active material and the particular therapeutic effect to be achieved, and (b) the limitations inherent in the art of compounding such an active material for the treatment of disorders in living subjects having a disordered condition, without excessive cytotoxic side effects.

Reduction in serum uric acid levels may be attained, for example, by the administration of daily doses of the 5-pyrimidinecarboxamides for up to five days, or longer. Multiple dosing, or dosing on any desired periodic basis, may also be utilized.

BEST MODE FOR CARRYING OUT THE INVENTION

The invention will be described in greater detail in connection with the following clinical study illustrating the reduction of serum uric acid levels by administration of the preferred 5-pyrimidinecarboxamide, merbarone, in accordance with the therapeutic method of the invention.

The efficacy of merbarone in reducing serum uric acid levels was determined in vivo in a number of patients. The drug was administered in separate courses, either by 24 hour continuous intravenous infusion for 5 days, or by daily two hour continuous infusions for 5 days. The daily dose ranged from 100 to 1000 mg/m$^2$.

The results obtained are summarized in the following table:

| CHANGE IN HUMAN SERUM URIC ACID LEVELS WITH MERBARONE | | | | |
|---|---|---|---|---|
| Dose mg/m$^2$/Day | # Evaluable Courses | Serum Uric Acid Concentration mg/dl | | |
| | | Initial | Lowest | Median Day |
| 100 | 5 | 5.7 ± 1.8 | 1.2 ± 0.4 | (6) |
| 150 | 3 | 5.3 ± 1.6 | 1.6 ± 0.5 | (3) |
| 200 | 2 | 5.2 ± 0.7 | 0.7 ± 0.1 | (3) |
| 250 | 2 | 5.8 ± 1.8 | 1.1 ± 0.3 | (5) |
| 300 | 3 | 6.6 ± 2.8 | 1.6 ± 0.8 | (3) |
| 400 | 2 | 4.7 ± 0.5 | 1.4 ± 0.6 | (5) |
| 500 | 2 | 5.1 ± 0.2 | 1.2 ± 0.1 | (5) |
| 750 | 1 | 9.0 | 1.4 | (5) |
| MEAN | | 5.7 ± 1.6 | 1.3 ± 0.5 | (5) |

A profound decrease in serum uric acid levels in patients treated with the indicated dosages (100 to 750 mg/m$^2$/day) was thus observed. Although phlebitis occurred in a number of cases, no other significant toxic factors were observed in the treatment with merbarone.

From the preceding it will be seen that, in accordance with the present invention, a method is provided for substantially reducing serum uric acid levels in mammals. It will be apparent that various changes may be made in the specific 5-pryimidinecarboxamides utilized in present method without departing from the scope of the invention. Accordingly, the preceding disclosure should be construed as illustrative only, and the scope of the invention should be interpreted in accordance with the claims appended hereto.

We claim:

1. A method for reducing serum uric acid levels in a mammal, which comprises administering to the mammal an effective amount of a compound of the formula:

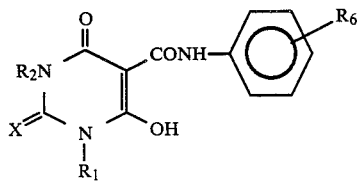

wherein $R_1$ and $R_2$ may each independently be hydrogen; alkyl, or phenyl, phenalkyl, phenalkenyl or phenalkynyl, the alkyl, alkenyl or alkynyl moieties of which have from one to six carbon atoms;

$R_6$ is at least one substituent selected from the group consisting of hydrogen; halogen; alkyl, alkenyl, alkynyl, alkoxy or phenyl, phenalkyl, phenalkenyl or phenalkynyl, the alkyl, alkenyl, alkynyl or alkoxy moieties of which have from one to six carbon atoms;

X is oxo or thioxo; and the pharmaceutically acceptable addition salts thereof.

2. A method for reducing serum uric acid levels in a mammal, which comprises administering to the mammal an effective amount of 1,2,3,4-tetrahydro-6-hydroxy-4-oxo-N-phenyl-2-thioxo-5-pyrimidinecarboxamide, or the pharmaceutically acceptable addition salts thereof.

* * * * *